United States Patent
Kardasz et al.

(10) Patent No.: US 9,950,967 B2
(45) Date of Patent: Apr. 24, 2018

(54) TITANIUM-CONTAINING FORMULATION AND METHOD OF PREPARATION OF TITANIUM-CONTAINING FORMULATION

(71) Applicant: INTERMAG Sp. z.o.o., Olkusz (PL)

(72) Inventors: Hubert Kardasz, Warszawa (PL); Tadeusz Czaja, Olkusz (PL); Adam Weglarz, Olkusz (PL)

(73) Assignee: INTERMAG Sp. z o.o., Olkusz (PL)

( * ) Notice: Subject to any disclaimer, the term of this patent is extended or adjusted under 35 U.S.C. 154(b) by 197 days.

(21) Appl. No.: 14/896,381

(22) PCT Filed: Oct. 10, 2013

(86) PCT No.: PCT/PL2013/000131
§ 371 (c)(1),
(2) Date: Dec. 5, 2015

(87) PCT Pub. No.: WO2015/016724
PCT Pub. Date: Feb. 5, 2015

(65) Prior Publication Data
US 2016/0130190 A1   May 12, 2016

(30) Foreign Application Priority Data

Jul. 29, 2013 (PL) .................................... P-404894

(51) Int. Cl.
| | | |
|---|---|---|
| *C05D 5/00* | (2006.01) | |
| *C05G 3/00* | (2006.01) | |
| *A01N 37/36* | (2006.01) | |
| *A01N 55/02* | (2006.01) | |
| *A01N 59/06* | (2006.01) | |
| *A01N 59/00* | (2006.01) | |
| *A01G 1/00* | (2006.01) | |
| *A01G 25/00* | (2006.01) | |
| *C05G 3/02* | (2006.01) | |

(52) U.S. Cl.
CPC ............... *C05D 5/00* (2013.01); *A01G 1/001* (2013.01); *A01G 25/00* (2013.01); *A01N 37/36* (2013.01); *A01N 55/02* (2013.01); *A01N 59/00* (2013.01); *A01N 59/06* (2013.01); *C05G 3/0076* (2013.01); *C05G 3/02* (2013.01)

(58) Field of Classification Search
None
See application file for complete search history.

(56) References Cited

FOREIGN PATENT DOCUMENTS

| | | | |
|---|---|---|---|
| CN | 101429068 | A | 4/2011 |
| CS | 259731 | B1 | 10/1988 |
| JP | S62249902 | A | 10/1987 |
| PL | 163688 | B1 | 4/1994 |
| PL | 172871 | B1 | 12/1997 |
| PL | 391564/PL21468B1 | A1 | 1/2012 |
| WO | 2005/118508 | A2 | 12/2005 |

OTHER PUBLICATIONS

I. Pais, The Biological Importance of Titanium, J. Plant Nutr. 6, 1983.
Mark A. Shand, Magnesium Hydroxide—A Safer Alternative to Caustic Soda (Sodium Hydroxide), Premier Chemicals, LLC, Jan. 1, 2007.

*Primary Examiner* — Wayne Langel
(74) *Attorney, Agent, or Firm* — Andrew Malarz

(57) ABSTRACT

A titanium-containing formulation contains complexes of titanium salts with an ascorbic acid and a citric acid, a preservative agent, and water-soluble sulfates of metals absorbable by plants, and optionally additional plant nutrients, in particular nitrogen and potassium. The titanium-containing formulation is a product of titanium complexation reaction of titanyl sulfate with a mixture of ascorbic acid and citric acid in aqueous environment alkalized with magnesium hydroxide in presence of acetic acid, at a mass ratio of magnesium, calculated as MgO, to titanium amounting from 1:1 to 20:1. Furthermore, in the titanium-containing formulation a mass ratio of the ascorbic acid to the citric acid amounts from 5:1 to 3:5, a mass ratio of the ascorbic acid to titanium amounts from 7:2 to 10:1, and a mass ratio of the magnesium hydroxide, calculated as MgO, to the acetic acid, calculated as 100% of the acetic acid, amounts from 8:1 to 3:5.

25 Claims, No Drawings

TITANIUM-CONTAINING FORMULATION AND METHOD OF PREPARATION OF TITANIUM-CONTAINING FORMULATION

CROSS-REFERENCE TO RELATED APPLICATIONS

This application is the national stage of the International Application No. PCT/2013/000131 claims pursuant to 35 U.S.C. 119 and the Paris Convention Treaty the benefit of Polish Patent Application No. P.404894 filed on Oct. 10, 2013, the contents of which are incorporated herein by reference.

BACKGROUND OF THE INVENTION

Field of the Invention

The invention relates to a titanium-containing formulation and a method of preparation of a titanium-containing formulation.

Brief Description of the Background of the Invention Including Prior Art

Titanium plays an important role in the stimulation of plant growth and development. As described by I. PAIS in his publication "The Biological Importance of Titanium" *J. Plant Nutr.* 6:3-133, 1983, titanium accelerates the biochemical processes, photosynthesis, and plant respiration, and increases the yield by 10-20% while limiting the development of certain diseases caused by fungi. The most preferable form of titanium use in agriculture and horticulture is a titanium complex with ascorbic acid and citric acid, as the resulting complex compounds are well soluble in water, quickly absorbed and non-toxic to plants.

From the description of the Polish patent PL 172871 B1, liquid fertilizer is known containing titanium and microelement salts complexed with ascorbic acid and citric acid. The content of microelements amounts in % by weight: titanium 0.05-0.25, the sum of manganese, molybdenum, zinc, iron 0.2-0.4, and 0.1-0.9 boron. Ascorbic acid and citric acid are introduced in the ratio of 1:(0.02-1).

From the Polish patent application PL 391564 A1, the manner of preparation of a titanium-containing fertilizer is also known, through the reaction of an aqueous solution of ascorbic acid with an alkali metal carbonate and complexing titanium from the aqueous solution of titanium salts. It consists in adding a solution of titanyl sulfate into the aqueous solution of sodium ascorbate and/or potassium having a pH above 9, after the introduction of the preservative in the form of sodium nitrite, and conducting the titanium complexing process until the pH is stabilized at the level of 5.5-6. Then, using additional complexing of titanium and mineral salts contained in the water is conducted through citric acid, and the pH of the formulated product is reduced to the level of 4.7-5.0. The invention also relates to a fertilizer agent, characterized in that it contains 5-10 g/l of titanium in the form of the following complexes: titanium ascorbate and titanium citrate, preferably in the ratio of 85:15, and ca. 0.4% addition of sodium nitrite. In addition, the present invention involves the use of the product as a fertilizer, to be used as crop spraying, in particular on cucumbers, tomatoes and eggplants in the period before and during flowering. The fertilizing agent is administered in the form of a working solution, at a dose of 0.2 l/ha, for vegetables such as tomatoes and cucumbers every 14 days from the moment the rooting of seedlings, and for cereals in three growth phases: tillering, stem elongation and heading. In addition, the agent is suitable for use in admixture with other multicomponent fertilizers, in an amount of 0.01-0.4% in the case of liquid fertilizers and of 0.01-0.05 in the case of crystalline fertilizers.

In turn, from the patent specification PL 163688 B1, the process for preparing the titanium formulation is known, consisting in the preparation of complexes of titanium salt with ascorbic acid, wherein the starting material containing ascorbic acid is introduced into water at 20° C., after which the resulting solution is separated from the environment preferably by adding a small amount of sodium carbonate. To so protected solution, the aqueous solution of titanium salts, preferably of titanyl sulfate is added, and then a small amount of a strong reducing agent, preferably in the form of a solution of titanium trichloride, and the mixture is stirred for 30 minutes. The resulting solution is subjected to neutralization first with a sodium hydroxide solution, and in the final stage with a sodium carbonate solution while maintaining the pH of the solution at a stable level of ca. 3.

The compounds of sodium used in the known solutions of neutralizing the acidic environment, such as sodium carbonate, sodium hydroxide, or mixtures thereof, form sodium sulfate, reacting with the sulfate group derived from the titanyl sulfate and sulfuric acid which stabilize the solution of titanyl sulfate against hydrolysis. This compound ($Na_2SO_4$), characterised by low solubility particularly at temperatures near zero degrees Celsius, makes it difficult to store the product at these temperatures, in particular at temperatures below 0° C. The aforesaid problem increases with increasing titanium content in the product, which is the result of using in the production of known formulations of increased amounts of a titanium carrier in the form of titanyl sulfate, which in turn increases the amount of sodium sulfate in the product. An additional disadvantage consists in the fact that with increasing titanium content, the sodium sulfate content in the product makes it impossible to introduce into known titanium formulations of additional plant nutrients, beneficial for the plants, due to the high degree of saturation of the solution.

Surprisingly, it was found that the problems with the low-temperature storage of the titanium formulation with a relatively high content of titanium can be prevented, and at the same time, a stable titanium product can be obtained which is easy to mix with other formulations used in the cultivation and fertilizers, if the sodium compounds, which are used in the known methods to neutralize the acidic environment during the complexing of titanium from titanyl sulfate with ascorbic acid and citric acid, is replaced by other metal compounds, preferably substances which are plant nutrients.

Surprisingly advantageous results were discovered by using magnesium hydroxide ($Mg(OH)_2$) in the present invention to neutralize the acidic environment during titanium complexing with a mixture of ascorbic acid and citric acid, as this allowed the complete removal of sodium from the titanium formulation, while enabling the introduction of magnesium, which is a nutrient necessary for the growth of plants, and the main component of chlorophyll, the green pigment of plants necessary in the process of photosynthesis and the activation of many enzymes.

In this solution, 1 mol of magnesium (24 g) introduced binds one sulfate group $(SO_4)^{-2}$ into magnesium sulfate ($MgSO_4$), while according to the known solutions, the neutralization of one mol of sulfate group into sodium sulfate ($Na_2SO_4$) requires introducing two moles of sodium, i.e. 46 g.

It turned out that the use of magnesium in the form of hydroxide unexpectedly allowed obtaining a very stable product, both in low and high temperatures. As shown by the results of physical and chemical tests, the titanium formulation thus obtained is stable in the range from −6 to +45° C. At the same time, the presence of titanium and magnesium in the composition favorably influenced the plant growth.

The essence of the invention consists in that in the known process of titanium complexing with a mixture of ascorbic acid and citric acid, magnesium hydroxide is used to neutralize free sulfate ions, which is at the same time a carrier of magnesium. Moreover, in the process of titanium complexing, acetic acid simultaneously is used as an advantageous preservative which also allows to significantly increase the magnesium content in the titanium formulation.

It also turned out that the presence of magnesium in the form of magnesium acetate in the titanium formulation according to the invention allows to eliminate the agents preventing the development of fungi on the surface of the product during storage which are used in other methods, which can be attributed to the fungicidal properties of acetates.

SUMMARY OF THE INVENTION

Purposes of the Invention

It is an object of the present invention to provide a titanium-containing formulation to increase growing of some plants, a method of preparation of the titanium-containing formulation and a use of the titanium-containing formulation in cultivation of plants as plant growth stimulator.

These and other objects and advantages of the present invention will become apparent from the detailed description, which follows.

Brief Description of the Invention

According to the invention, a titanium-containing formulation containing complexes of titanium salts with ascorbic acid and citric acid, a preservative agent, and water-soluble sulfates of metals absorbable by plants, and optionally additional plant nutrients, in particular nitrogen and potassium, characterized in that it comprises the product of the titanium complexation reaction from titanyl sulfate with a mixture of ascorbic acid and citric acid in aqueous environment alkalized with magnesium hydroxide, in the simultaneous presence of acetic acid, at the following mass ratio: magnesium (calculated as MgO) to titanium of 1:1 to 20:1; ascorbic acid to citric acid of 5:1 to 3:5, preferably 2:1; ascorbic acid to titanium of 7:2 to 10:1, preferably 4:1 to 6:1; and magnesium hydroxide (calculated as MgO) to acetic acid (calculated as 100% acetic acid) of 8:1 to 3:5.

The formulation is characterized in that in the liquid form, it has a pH of 2.5 to 5.5 and preferably contains between 2 and 25 g Ti/l and up to 170 g MgO/l. For performance reasons, it is preferable that the content of titanium in the liquid formulation be of 8.5 g Ti/l, and of magnesium 62-65 g MgO/l.

The powdery formulation, on the other hand, obtained by drying the liquid form, is characterized in that it comprises titanium up to 65 g Ti/kg and magnesium up to 200 g MgO/kg.

A method of the preparation of a titanium-containing formulation, comprising according to the invention of at least producing complexes of titanium salts with ascorbic acid and citric acid as titanium complexing agents in an aqueous environment with the use of titanyl sulfate as the source of a titanium, using of an alkalizing agent of acidic environment resulting from the introduction of ascorbic acid, citric acid and titanyl sulfate, using of a preservative agent, and optionally using of a pH regulator, and packaging the formulation solution and/or drying it, is characterized in that magnesium hydroxide is used as the alkalizing agent of the acidic environment of the titanium complexation reaction, and acetic acid simultaneously is used as a preservative which allows to increase the magnesium content in the titanium formulation, wherein in accordance with the invention, titanium ascorbate and titanium citrate are obtained by the complexation of titanyl sulfate in the aqueous suspension containing magnesium hydroxide, ascorbic acid and citric acid at a mass ratio of magnesium (calculated as MgO) to titanium (Ti) of 1:1 to 20:1, in the presence of acetic acid.

For this purpose in the present invention, after the introduction of magnesium hydroxide into the water and obtaining a homogeneous suspension, carboxylic acids, i.e. ascorbic acid, citric acid, and acetic acid are introduced, in such a mass ratio that the ratio of ascorbic acid to citric acid is of 5:1 to 3:5, preferably 2:1; the ratio of ascorbic acid to titanium is of 7:2 to 10:1, preferably between 4:1 and 6:1; and the ratio of magnesium hydroxide (calculated as MgO) to the amount of acetic acid (calculated as 100% acetic acid) is of 8:1 to 3:5.

After the complete dissolution of carboxylic acids in the suspension and their partial reaction of magnesium hydroxide, while maintaining the temperature preferably in the range 50-60° C., a slow stream of a solution of titanyl sulfate is introduced and the mixture is stirred until obtaining a clear brown solution having a pH of 2.5-5.5.

As the titanyl sulfate ($TiOSO_4$) contains significant amounts (390-490 g/l) of free sulfuric acid, which protects the sulfate from possible hydrolysis (as a result of which titanium dioxide ($TiO_2$) with low reactivity is created), carboxylic acids are introduced into the reaction environment containing magnesium hydroxide before the introduction of titanyl sulfate in order to prevent the creation of insoluble titanium oxides.

After complete reaction and dissolution of the components added, optionally the final pH of the liquid titanium formulation is regulated by the addition of agents such as citric acid and/or acetic acid, monoethanolamine, hydroxides and/or carbonates of metals, preferably potassium.

It is preferable to use monoethanolamine (colamine) for the final pH adjustment because it has an additional property of sequestering nutrients, and additionally has a positive effect on lowering the surface tension of both the produced titanium formulation and the so-called "working solutions" prepared on its basis and used for spraying plants.

The resulting liquid titanium formulation is finally directed to packaging or the drying process. The drying of the liquid formulation is preferably performed by the spray method.

The use of magnesium hydroxide in the process according to the present invention was found to be surprisingly advantageous. This allowed the complete removal of sodium compounds: sodium hydroxide and/or carbonate, which were used in the known solutions in order to bind the sulfate groups of free sulfuric acid and the sulfate groups formed from the titanyl sulfate during the titanium complexation with ascorbic acid and citric, and additionally the use of magnesium hydroxide allowed for pH control of the finished product.

Magnesium hydroxide, used in this process as the alkalizer of the titanium complexation reaction environment, and also as a carrier of magnesium, binds free sulfuric acid contained in the titanium source provided by the solution of titanyl sulfate and the sulfate groups created in the process of titanium complexation.

It has proved advantageous to use acetic acid to protect the formed product against the development of fungi as well as adjust the pH of the finished formulation. At the same time, the use of acetic acid as a preservative agent allowed to introduce significant amounts of magnesium (up to 170 g of MgO)/l) into the titanium formulation obtained, as a result of producing magnesium acetate by reaction with magnesium hydroxide.

The liquid titanium formulation prepared by the method according to the invention, depending on the amount of titanyl sulfate used, comprises preferably between 2 and 25 g of Ti/l and up to 170 g MgO/l.

For performance reasons, it is preferable when in the method according to the invention, titanyl sulfate is used in an amount such that the titanium content in the final formulation is of 8.5 g Ti/l, and magnesium content (calculated as MgO) 62-65 g MgO/l.

The powdery formulation, on the other hand, obtained by the method according to the invention after drying the liquid form, has a titanium content of up to 65 g Ti/kg and magnesium content of up to 200 g MgO/kg.

Both the liquid and the powdery formulation can be used as a component in the production of fertilizers or other agrochemicals, due to its stability and good miscibility.

It was found that it is unexpectedly beneficial for plant growth to use of the titanium formulation according to the invention as defined above, wherein the composition of both titanium and magnesium are present simultaneously.

It turned out that the use of the titanium formulation according to the invention in the cultivation of plants, after previous dilution in water, for the foliar feeding of crops gives unexpectedly beneficial effects for the stimulation of plant growth, which is also an object of the present invention.

According to the invention, the use of the titanium-containing formulation in the cultivation of plants as plant growth stimulator, which formulation contain the product of titanium complexing reaction from titanyl sulfate with a mixture of ascorbic acid and citric acid in aqueous environment alkalized with magnesium hydroxide, in the simultaneous presence of acetic acid, at the following mass ratio: magnesium (calculated as MgO) to titanium of 1:1 to 20:1; ascorbic acid to citric acid of 5:1 to 3:5, preferably 2:1; ascorbic acid to titanium of 7:2 to 10:1, preferably 4:1 to 6:1; and magnesium hydroxide (calculated as MgO) to acetic acid (calculated as 100% acetic acid) of 8:1 to 3:5, consists in that, that the liquid formulation, after dilution in water, and the powdery formulation, after dissolution in water, is fed to plants in the form of foliar spray treatments, or fertigation, at a dose of preferably 1.7 to 5.5 g Ti/ha (i.e. the dose of 0.2-0, 6 l/ha, with the use of a liquid formulation containing 8.5 g Ti/l), wherein the treatment is carried out in 2-4 daily doses, the first of which is administered at the beginning of plant vegetation, and further ones every 10-14 days.

When using the formulation according to the invention, it may be preferable to add other macro- and/or microelement fertilizers, or mixtures thereof, as well as previously diluted plant protection products (pesticides) to the diluted formulation solution, prepared to carry out foliar spraying of plants or fertigation.

The invention ensures obtaining a formulation the use of which leads to activating the intensity of photosynthesis and nutrient uptake by crops, in particular cereals and oilseed rape, administered both on the leaves and from the soil, as confirmed by many years of tests conducted on experimental plots.

High content of components advantageous to plants were achieved in the formulation according to the invention thanks to the complete elimination of sodium carbonate and/or sodium hydroxide, which were used in many prior art methods for alkalizing the environment of the titanium complexation reaction with ascorbic and citric acids, and moreover thanks to the introduction of magnesium hydroxide ($Mg(OH)_2$) replacing sodium compounds as a regulator of the environment of the titanium complexation reaction, and which is simultaneously a magnesium carrier and the control of the final pH of the product obtained, and finally the use of mixtures of organic (carboxylic) acids: citric, ascorbic and acetic acid.

It is known that in the existing methods, the sodium compounds are used to neutralize the acidic environment to form sodium sulfate with sulfate groups, i.e. a compound ($Na_2SO_4$) with low solubility in water, in particular at low temperatures, which made it difficult to store the titanium formulation at temperatures below 0° C. Furthermore, the high content of sodium sulfate did not permit the introduction of other nutrients, in this case magnesium, which is necessary for plant growth, because of the high degree of saturation of the solution.

It is well known that magnesium, the main component of chlorophyll, the green pigment of plants necessary for the process of photosynthesis and the activation of many enzymes, is responsible for the formation of chlorophyll and photosynthesis of the plant, and is an activator of many enzymes, while titanium plays an important role in the stimulation of plant growth and development.

However, unexpectedly favorable results for the stimulation of plant growth are obtained by the simultaneous presence in the formulation according to the invention of a composition of titanium and magnesium in the mutual proportions as described above.

All the above mentioned characteristics of the formulation according to the invention result in the fact that the feeding of plants in agricultural and horticultural crops, particularly in the foliar form, with properly diluted titanium formulation allows for increased yields and better quality.

The resulting formulation has a high stability at low and high storage temperatures, and at the same time a good miscibility with macro- and micro-element fertilizers and plant protection products. These properties create a high potential to form a number of new fertilizer combinations, whether in the liquid or powdery form, which are both easily soluble in water.

The diluted solutions of the fertilizer mixtures with the titanium formulation according to the invention have a high stability over time, and a wide range of pH values.

DESCRIPTION OF INVENTION AND PREFERRED EMBODIMENTS

The invention is explained in detail in the following examples. These examples should not, however, be perceived to limit the essence of the invention or reduce the scope of invention protection, since they are only provided as an illustration.

EXAMPLE 1

This example illustrates the preparation of the liquid titanium formulation containing 8.5 g Ti/l and 35 g MgO/l.

720 liters of water at the temperature of 20° C. were poured into a stirred tank reactor with the possibility of cooling, and after starting the stirrer, 52.0 kilograms of magnesium hydroxide were added in portions. After obtaining a homogeneous suspension, 17.0 kg of citric acid were added, and after 30 minutes, 46.0 kg of ascorbic acid. After its dissolution, 170.0 kg of a titanyl sulfate solution containing 50.0 g of Ti/kg (Ti content 67 g/l) was added in a thin stream. In this manner, reaction mixture with a pH of 7.8 was obtained in the form of a suspension of magnesium hydroxide in a solution of the obtained complex of titanium and magnesium sulfate. To the reaction mixture obtained in this way, 80% acetic acid in an amount of 9.5 liters was added in a thin stream. Dosing was carried out while cooling the reaction mixture and maintaining the temperature of 55-60° C. After 50 minutes of conducting the process and the addition of water up to 1000 liters, a product in the form of a clear, dark brown solution having a final pH of 4.5 was obtained. The final product pH was adjusted by adding 1.2 kg of citric acid. After cooling and standing the titanium formulation obtained was filtered and then packaged.

EXAMPLE 2

This example illustrates the preparation of a liquid titanium formulation containing 17 g Ti/l and 124 MgO g/l.

In a tank (as specified above for Example 1), 71.0 kg of citric acid, and then 90.0 kg of ascorbic acid were dissolved in 320 liters of water. After their dissolution, 185.5 kg of magnesium hydroxide were slowly added in small portions while cooling, and after having obtained a homogeneous suspension, a thin stream of 80% acetic acid in an amount of 320.0 liters was dosed very slowly so as not to exceed the temperature of 60° C. After 45 minutes of stirring, 185.2 liters of titanyl sulfate solution containing 92.3 g Ti/l were added. As in the case of acetic acid dosing, due to the highly exothermic nature of the process, the addition of titanyl sulfate was carried out slowly and in small amounts, cooling the reaction mixture to a temperature of 55-60° C. The final pH was adjusted by adding acetic acid in an amount of 2.5 l.

EXAMPLE 3

This example illustrates the preparation of the powdery titanium formulation with a content of 5.5% Ti and 6.5% MgO.

In a tank (as specified above) containing 800 liters of water at the temperature of 20° C., 46.0 kg of ascorbic acid and 20.0 kg of citric acid were dissolved. To, in this way obtained carboxylic acid solution, 15.0 kg of magnesium hydroxide were introduced in small portions. While continuously stirring, after the completion of the reaction, magnesium hydroxide was added, and obtaining a clear solution, 94.0 l of a solution of titanyl sulfate containing 92.0 g Ti/l were added in a thin stream. The process was conducted for a period of 50 minutes, after which time, 20.0 kg of potassium carbonate were added until obtaining a pH of 4.5. After obtaining a stable pH and a clear solution, the process was finished, and the solution containing 8.5 g Ti/l and 10.1 g MgO/l was filtered and subjected to a drying process in a fluidized bed dryer. The titanium formulation was obtained in the form of fine granules containing 5.5% Ti and 6.5% MgO by weight (i.e. 55 g Ti/kg and 65 g MgO/kg).

EXAMPLE 4

This example illustrates the use of the titanium formulation in the cultivation of wheat and oilseed rape.

Confidential experiments were conducted by the Agrochemistry and Plant Feeding Faculty of the Slovak Agricultural University in Nitra in the following years (seasons): 2009/2010, 2010/2011 and 2011/2012 on experimental plots located in the town of Bučany in Slovakia.

Experiments were conducted on the Šarlota winter wheat variety and the Chagall winter oilseed rape variety. The experiments consisted in the use of the titanium formulation according to the invention, containing 8.5 g T/l and 62 g of MgO/l on plots of the surface of 20 m² on four occasions in four different combinations. The best results were obtained by using foliar spraying for the formulation dose of 0.2 liter/ha in three treatments:

In the case of wheat, the first procedure was performed in the BBCH 29 stage (end of tillering), the second procedure was performed in the BBCH 32 stage (stem elongation) and the third procedure was performed in the BBCH 55-59 stage (heading).

In the case of oilseed rape, the first procedure was performed in the BBCH 50-53 stage (green bud), the second procedure was performed in the BBCH 59 stage (yellow bud), and the third procedure was performed in the BBCH 66-67 stage (flowering).

The experiments conducted during three seasons demonstrated:
increase in wheat yield by an average of 8%-15%;
increase in oilseed rape yield by an average of 13%-24%.

The experiments confirmed that it is advantageous for plants to use in crop growth water-diluted formulation according to the invention in the form of foliar spraying, at a dose of at least 1.7 Ti/ha (i.e. in the dose of 0.2 l/ha with the use of a liquid formulation containing 8.5 Ti g/l) in three sprayings, the first of which is performed at the beginning of plant vegetation (the "end of tillering" stage for wheat and the "green bud" stage for oilseed rape) and the following ones in intervals of 10-14 day (until the "heading" stage for wheat and the "flowering" stage for oilseed rape).

What is claimed is:

1. A titanium-containing formulation containing complexes of titanium salts with an ascorbic acid and a citric acid, a preservative agent, and water-soluble sulfates of metals absorbable by plants, and optionally additional plant nutrients, is a product of titanium complexation reaction of titanyl sulfate with a mixture of ascorbic acid and citric acid in aqueous environment alkalized with magnesium hydroxide in simultaneous presence of acetic acid, at a mass ratio of magnesium, calculated as MgO, to titanium amounting from 1:1 to 20:1 wherein a mass ratio of the ascorbic acid to the citric acid amounts from 5:1 to 3:5 and wherein a mass ratio of the ascorbic acid to titanium amounts from 7:2 to 10:1 and a mass ratio of the magnesium hydroxide, calculated as MgO, to the acetic acid, calculated as 100% acetic acid, amounts from 8:1 to 3:5.

2. The titanium-containing formulation according to claim 1, wherein the titanium-containing formulation in a liquid form has a pH of 2.5 to 5.5.

3. The titanium-containing formulation according to claim 1, wherein a liquid form of titanium-containing formulation contains between 2 and 25 g Ti/l and magnesium in an amount of up to 170 g MgO/l.

4. The titanium-containing formulation according to claim 1, wherein a liquid form of titanium-containing formulation contains 8.5 g Ti/l and magnesium in an amount of 62-65 g MgO/l.

5. The titanium-containing formulation according to claim 4, wherein the titanium-containing formulation contains potassium and/or nitrogen.

6. The titanium-containing formulation according to claim 1, wherein a powdery form of titanium-containing formulation contains up to 65 g Ti/kg and magnesium in an amount of up to 200 g MgO/kg.

7. The titanium-containing formulation according to claim 6, wherein the titanium-containing formulation contains potassium and/or nitrogen.

8. The titanium-containing formulation according to claim 1, wherein the titanium-containing formulation is a product of titanium complexation reaction from titanyl sulfate with a mixture of ascorbic acid and citric acid in aqueous environment alkalized with magnesium hydroxide in presence of acetic acid at a mass ratio of magnesium, calculated as MgO, to titanium amounting from 1:1 to 20:1, wherein a mass ratio of the ascorbic acid to the citric acid amounts 2:1 and wherein a mass ratio of the ascorbic acid to titanium amounts from 4:1 to 6:1 and a mass ratio of the magnesium hydroxide, calculated as MgO, to the acetic acid, calculated as 100% of the acetic acid, amounts from 8:1 to 3:5.

9. The titanium-containing formulation according to claim 8, wherein the titanium-containing formulation in a liquid form has a pH of 2.5 to 5.5.

10. The titanium-containing formulation according to claim 8, wherein a liquid form of titanium-containing formulation contains between 2 and 25 g Ti/l and magnesium in an amount of up to 170 g MgO/l.

11. The titanium-containing formulation according to claim 8, wherein a liquid form of titanium-containing formulation contains 8.5 g Ti/l and magnesium in an amount of 62-65 g MgO/l.

12. The titanium-containing formulation according to claim 8, wherein a powdery form of titanium-containing formulation contains up to 65 g Ti/kg and magnesium in an amount of up to 200 g MgO/kg.

13. A method of preparation of a titanium-containing formulation, the method comprising
producing complexes of titanium salts with an ascorbic acid and an citric acid as titanium complexing agents in an aqueous environment using titanyl sulfate as a source of a titanium and using an alkalizing agent of acidic environment of titanium complexation reaction, and using a preservative agent, and optionally using a pH regulator; and
packaging a titanium-containing formulation solution and/or drying the titanium-containing formulation solution, wherein magnesium hydroxide is used as an alkalizing agent of an acidic environment of titanium complexation reaction, and the acetic acid simultaneously is used as a preservative which increase magnesium content in titanium-containing formulation solution, wherein complex titanium compounds with the ascorbic acid and the citric acid are obtained by complexation of titanyl sulfate in an aqueous suspension containing magnesium hydroxide, the ascorbic acid and the citric acid, in simultaneous presence of acetic acid, at a mass ratio of magnesium, calculated as MgO, to titanium amounting from 1:1 to 20:1, wherein a mass ratio of the ascorbic acid to the citric acid amounts from 5:1 to 3:5 and wherein a mass ratio of the ascorbic acid to titanium amounts from 7:2 to 10:1, and a mass ratio of the magnesium hydroxide, calculated as MgO, to the acetic acid, calculated as 100% acetic acid, amounts from 8:1 to 3:5.

14. The method according to claim 13, wherein the ascorbic acid, the citric acid and the acetic acid are introduced into a homogeneous aqueous suspension of magnesium hydroxide, and after their complete dissolution in the suspension and partial reaction with magnesium hydroxide, while maintaining temperature in a range 50-60° C., a titanyl sulfate solution is introduced in a slow stream and a mixture is stirred until a clear brown titanium-containing solution with a pH of 2.5 to 5.5 is obtained, and then a final pH of liquid titanium-containing formulation is regulated by addition of the citric acid, the acetic acid, monoethanolamine, or hydroxides or, carbonates of metals.

15. The method according to claim 14, wherein a final pH of the titanium-containing formulation solution is adjusted by using monoethanolamine.

16. The method according to claim 14, wherein the titanium-containing formulation solution is packaged.

17. The method according to claim 14, wherein the titanium-containing formulation solution is dried by a spray method.

18. The method according to claim 14, wherein the titanium-containing formulation is dried by a spray method.

19. The method according to claim 13, wherein complexation of titanyl sulfate is performed in an aqueous suspension containing magnesium hydroxide, the ascorbic acid and the citric acid in presence of acetic acid at a mass ratio of magnesium, calculated as MgO, to titanium amounting from 1:1 to 20:1, wherein a mass ratio of the ascorbic acid to the citric acid amounts 2:1 and wherein a mass ratio of the ascorbic acid to titanium amounts from 4:1 to 6:1 and a mass ratio of the magnesium hydroxide, calculated as MgO, to the acetic acid, calculated as 100% of the acetic acid, amounts from 8:1 to 3:5.

20. The method according to claim 19, wherein the ascorbic acid, the citric acid and the acetic acid are introduced into a homogeneous aqueous suspension of magnesium hydroxide, and after their complete dissolution in the homogeneous aqueous suspension and partial reaction with magnesium hydroxide, while maintaining temperature preferably in a range 50-60° C., a titanyl sulfate solution is introduced in a slow stream and a mixture is stirred until a clear brown titanium-containing solution with a pH of 2.5 to 5.5 is obtained, and then a final pH of liquid titanium-containing formulation is regulated by addition of potassium.

21. The method according to claim 19, wherein monoethanolamine is used to adjust a final pH of the titanium-containing formulation solution.

22. The method according to claim 19, wherein the titanium-containing formulation solution is directed to packaging.

23. The method according to claim 13, wherein the ascorbic acid, the citric acid and the acetic acid are introduced into a homogeneous aqueous suspension of magnesium hydroxide, and after their complete dissolution in the suspension and partial reaction with magnesium hydroxide, while maintaining temperature in a range 50-60° C., a titanyl sulfate solution is introduced in a slow stream and a mixture is stirred until a clear brown titanium-containing solution with a pH of 2.5 to 5.5 is obtained.

24. The method according to claim 23, wherein a final pH of the titanium-containing formulation solution is adjusted by using monoethanolamine.

25. The method according to claim 23, wherein the titanium-containing formulation solution is packaged.

* * * * *